US007766810B2

(12) United States Patent
Ohdaira

(10) Patent No.: US 7,766,810 B2
(45) Date of Patent: Aug. 3, 2010

(54) PROBING METHOD AND HOLDING METHOD FOR LUMINAL ORGAN

(75) Inventor: Takeshi Ohdaira, Kumagaya (JP)

(73) Assignee: Olympus Medical Systems Corp., Tokyo (JP)

( * ) Notice: Subject to any disclaimer, the term of this patent is extended or adjusted under 35 U.S.C. 154(b) by 981 days.

(21) Appl. No.: 11/076,662

(22) Filed: Mar. 10, 2005

(65) Prior Publication Data

US 2007/0004958 A1    Jan. 4, 2007

(51) Int. Cl.
*A61M 37/00*    (2006.01)
*A61B 1/00*    (2006.01)
*A61B 19/00*    (2006.01)

(52) U.S. Cl. .......................... 600/12; 600/104; 128/899
(58) Field of Classification Search ................. 128/899; 600/37, 12, 104; 604/175; 606/153
See application file for complete search history.

(56) References Cited

U.S. PATENT DOCUMENTS

| 3,986,493 | A | * | 10/1976 | Hendren, III | 600/12 |
| 5,330,486 | A | * | 7/1994 | Wilk | 606/139 |
| 5,690,656 | A | * | 11/1997 | Cope et al. | 606/153 |
| 6,632,229 | B1 | * | 10/2003 | Yamanouchi | 606/153 |
| 6,656,194 | B1 | * | 12/2003 | Gannoe et al. | 606/153 |
| 6,719,768 | B1 | * | 4/2004 | Cole et al. | 606/153 |
| 7,608,038 | B2 | * | 10/2009 | Ginsberg | 600/104 |
| 2004/0050395 | A1 | * | 3/2004 | Ueda et al. | 128/899 |
| 2005/0165272 | A1 | * | 7/2005 | Okada et al. | 600/114 |

FOREIGN PATENT DOCUMENTS

| JP | 2002-159508 | 6/2002 |
| WO | WO99/02098 | 1/1999 |

OTHER PUBLICATIONS

Machine Translation of W099/002098, from http://dossier.ipdl.inpit.go.jp/text_trans.html.*
Journal of Japan Surgical Society, vol. 105, Extra Edition, 2004.

* cited by examiner

*Primary Examiner*—Linda C Dvorak
*Assistant Examiner*—Alireza Nia
(74) *Attorney, Agent, or Firm*—Scully, Scott, Murphy & Presser, P.C.

(57) ABSTRACT

The present invention enables the desired area on a luminal organ to be held correctly during laparotomy or laparoscopic surgery, even without carrying out dot inking which requires a high degree of skill. In the present invention, a magnetic body is pre-anchored at a specific position inside a luminal organ. During surgery, a magnet is brought close to the outside of the luminal organ, such that the magnetic body is adsorbed to the magnet, along with the body tissue of the luminal organ, enabling traction.

6 Claims, 13 Drawing Sheets

PROBING METHOD AND HOLDING METHOD FOR LUMINAL ORGAN

BACKGROUND OF THE INVENTION

1. Field of the Invention

The present invention relates to a method for probing a specific site on the inner surface of a luminal organ within a body cavity, and to a method for holding the same luminal organ, during laparotomy or laparoscopic surgery.

2. Description of Related Art

A dot inking method employing India ink is carried out as a method for identifying microscopic lesions occurring on the inside of a luminal organ, such as the stomach or large intestine, during surgery via laparoscopy or laparotomy. In this dot inking method, India ink, which serves as a marker near the lesion, is injected from inside the luminal organ, to facilitate identification of the location of the lesion during either direct or indirect gross visualization of the outside of the luminal organ. A surgical method in which a lesion site occurring on the inside of the stomach is resected will now be explained as one example of this dot inking method.

First, several days to several weeks prior to the surgery, dot inking, which will serve as a marker during the resection, is performed near the site of the lesion. Specifically, an endoscope is inserted into the patient via the oral cavity, a needle is used to pierce the stomach wall from the inside near the lesion site, and India ink is injected. The injected India ink spreads out over the stomach wall, and assists in the direct or indirect gross confirmation of the lesion at the time of resection. During this procedure, care must be exercised to inject the ink to just the right depth to enable visual confirmation of the location of the spread India ink when viewing the stomach from the outside, without sticking the end of the needle completely through the stomach wall. If the needle penetrates through the stomach wall, then not only does the site of the lesion become unclear, but other internal organs may become coated with the India ink, resulting in a situation in which it is not possible to continue with surgery. Further, if the India ink cannot be injected so as to be visible from outside the stomach, then it is not possible to discern the lesion site, which can result in the all or part of the lesion being left behind following resection. In other words, the problem with this dot inking method is that it requires a high level of expertise to adjust the depth to which the needle is pierced, so that the dot inking can be carried out reliably.

Next, a conventional method for holding the lesion site as required during surgery will be explained. During surgery, the surgeon first searches for the location of the dot inking while using a laparoscope to visualize the outside of the stomach. Once the position of the dot inking is found, the positional relationship between the dot inking and the lesion site is taken into consideration, and metallic holding forceps are employed to hold the stomach and apply traction in a manner that will enable resection. Then, at a location on the stomach that is separated away from the area being held, a portion of the stomach (that includes the lesion site) is cut out using a procedure tool such as an automatic suturing device. In order that none of the lesion site is left behind in this method, it is necessary that the surgeon separate the lesion site and the holding position in this method. Additionally, since the surgeon must simultaneously carry out confirmation of the lesion site and the operation of holding the lesion, a high level of expertise is demanded.

As another method for resecting the stomach, there is a method in which, instead of using metallic holding forceps to hold the stomach in the vicinity of the lesion, the area of the stomach near the lesion is instead suspended using a thin metal rod in which a wire has been attached to the center, and the suspended area is resected. More specifically, this metal rod with attached wire is passed through the stomach wall by piercing the outside of the stomach with the rod in the vicinity of the lesion, which has been inked. Next, the wire attached to the metal rod is introduced to the outside of the abdominal cavity. Then, by applying traction from outside the body on the wire attached to the metal rod, the lesion site on the stomach can be suspended, and the lesion site, which is now easily resectable as a result of being suspended, is resected using an automatic incising and suturing device. This method requires a high level of skill to perform the operation of piercing the metal rod with the attached wire near the lesion from a position outside the body.

SUMMARY OF THE INVENTION

The present invention provides a method for probing a luminal organ that is provided with the steps of:
pre-anchoring a magnetic body at a specific position inside a luminal organ; and
bringing a magnet close to the outside of the luminal organ, such that the magnetic body is attracted to the magnet, along with the body tissue of the luminal organ.

The present invention provides a method for holding a luminal organ that is provided with the steps of:
pre-anchoring a magnetic body at a specific position inside a luminal organ; and
bringing a magnet close to the outside of the luminal organ, such that the magnetic body is pulled and held to the magnet, along with the body tissue of the luminal organ.

The present invention provides a method for changing between applications that is provided with a step for switching between the above-described probing method for a luminal organ and the above-described holding method for a luminal organ by adjusting the strength of the magnetic force of the magnet.

DESCRIPTION OF THE PREFERRED EMBODIMENTS

Embodiment 1

The surgery to partially resect the stomach under laparoscopy will be explained in this embodiment with reference to FIGS. 1 through 9.

Figure 1:
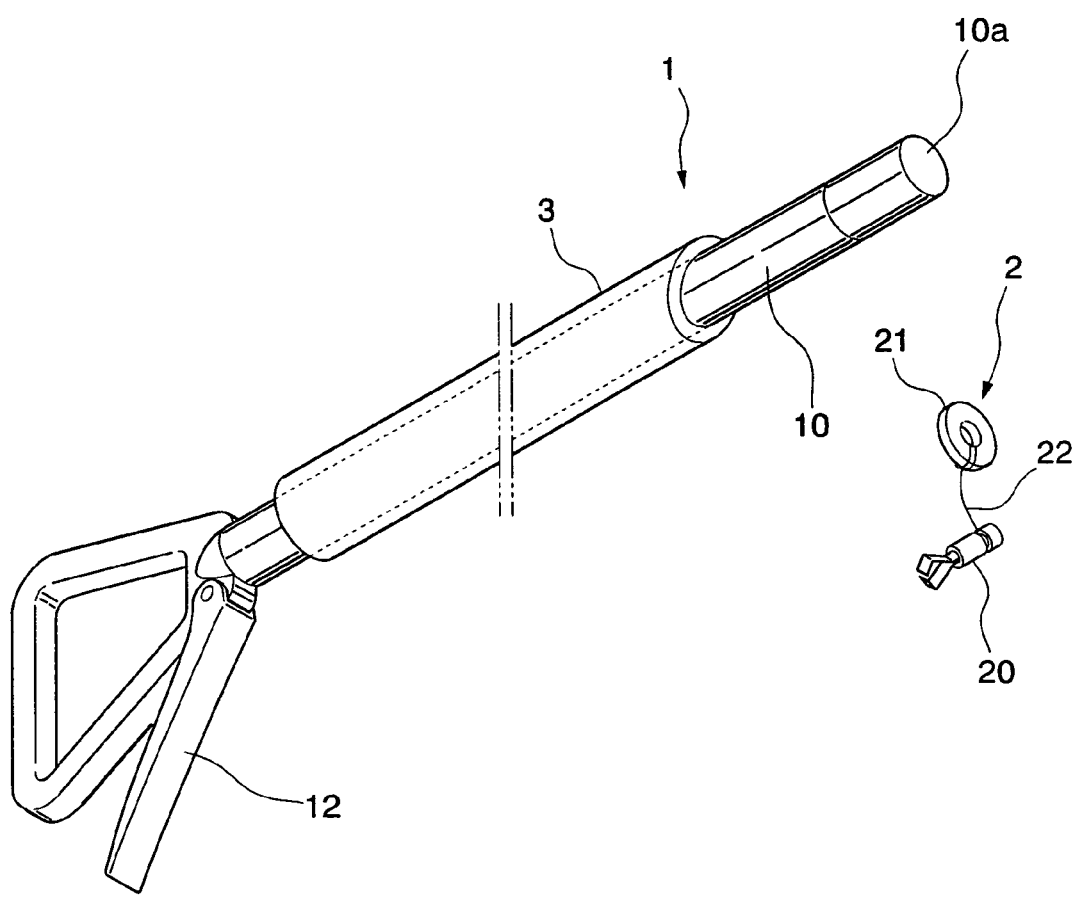
FIG. 1 is a perspective view showing a magnetic forceps and anchoring device employed in the surgery according to the present invention.
Figure 2:
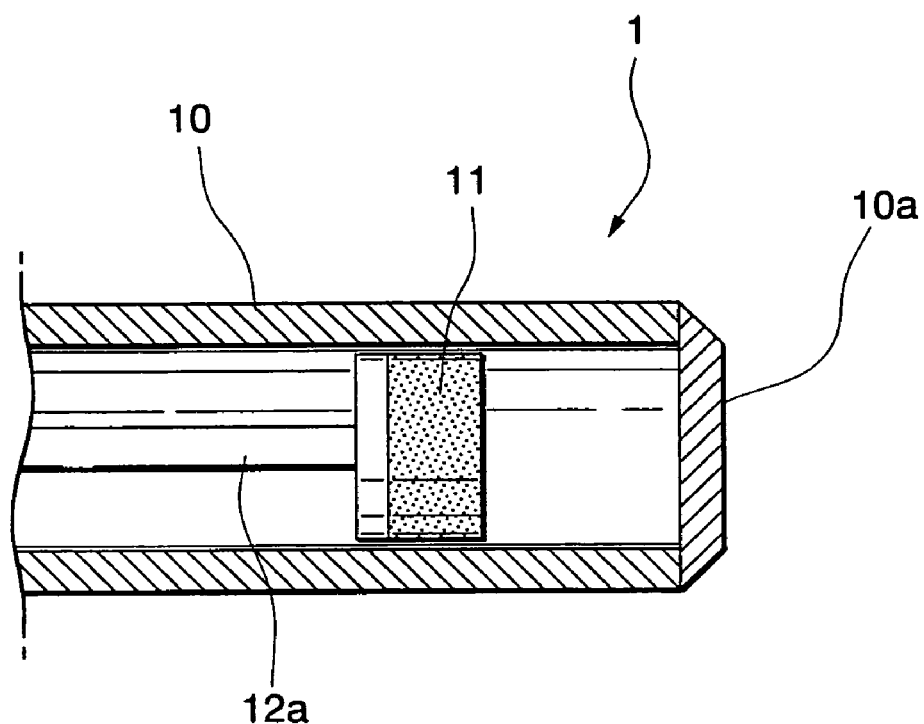
FIG. 2 is a cross-sectional view showing an essential element of the magnetic forceps.
Figure 3:
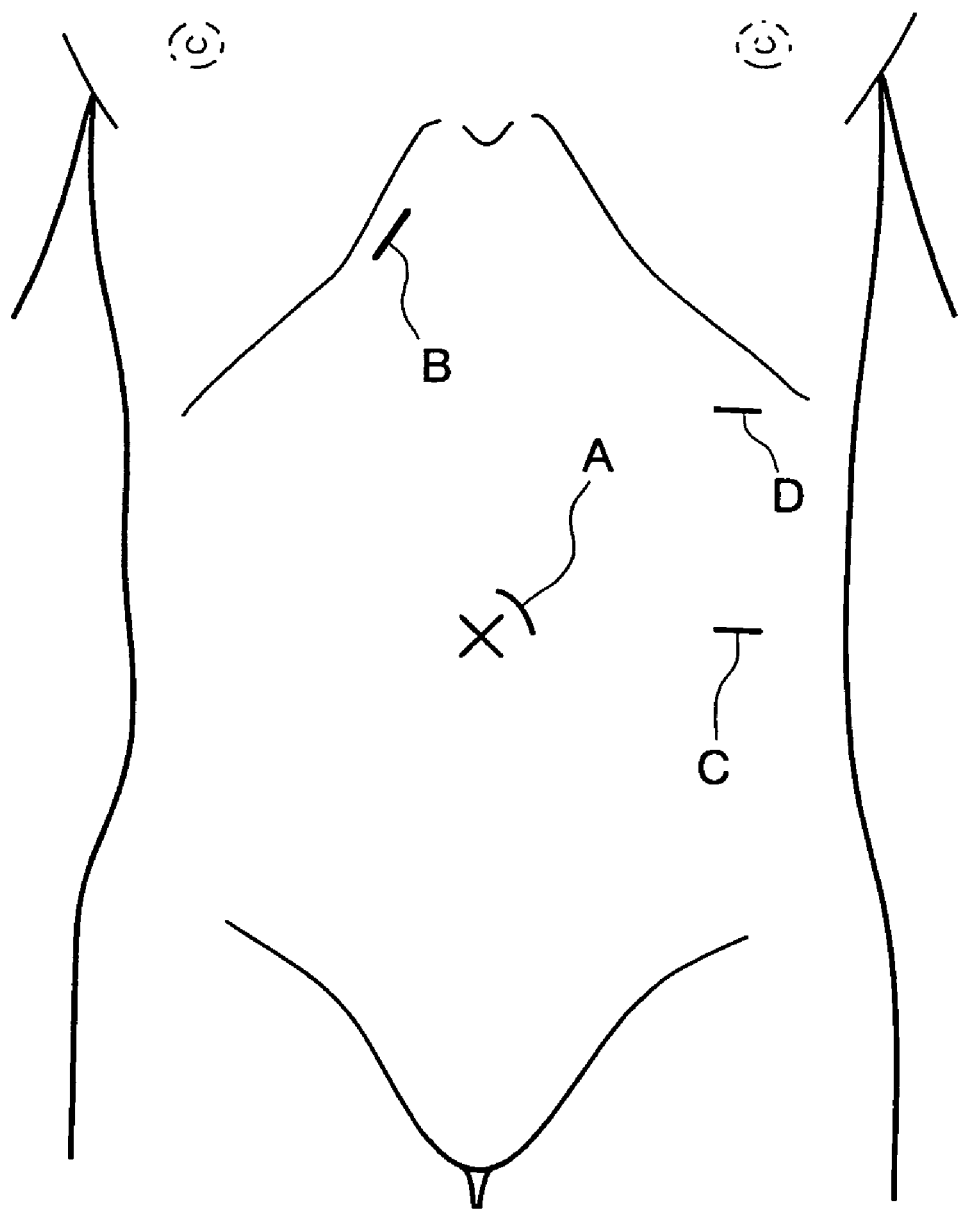
FIG. 3 is a view showing the position of the penetrating holes that are made in the abdomen of the patient during the surgery according to the present invention.

The instruments employed in the surgery will be explained first. FIGS. 1 and 2 show a magnetic forceps 1 and an anchoring device 2, which is anchored on the inside of the stomach, that are employed in the partial resection of the stomach in this embodiment. Magnetic forceps 1 is provided with an inserted part 10 which is inserted into the abdominal cavity, a magnet 11 for attracting and contacting anchoring device 2, and an operating part 12 for operating magnet 11. Inserted part 10 is in the form of a rigid narrow tube, the end of which is covered by fixing in place a cover 10a.

Magnet 11 is cylindrical in shape and has an outer diameter that is slightly smaller than the inner diameter of inserted part 10. One end surface thereof forms the N pole, and the other end surface thereof forms the S pole. The magnetic line of force magnet 11 acts to pass through both end surfaces. Magnet 11 is seated inside of the end of inserted part 10, and is disposed so as to move along the longitudinal direction of inserted part 10. Operating part 12 is provided at the base end of inserted part 10. Operating part 12 is connected to magnet 11 via a rod 12a that is disposed inside inserted part 10.

By manipulating operating part 12 of magnetic forceps 1, it is possible to adjust the strength of the magnetic force generated at the end of inserted part 10. Specifically, when rod 12a is pulled out from inserted part 10 by manually manipulating operating part 12, magnet 11 is moved in a direction away from cover 10a on the inside of inserted part 10. In this case, the magnetic flux density at the end of magnetic forceps 1 decreases, and the magnetic force generated at the end of inserted part 10 weakens. On the other hand, by pushing rod 12a into inserted part 10, magnet 11 is moved in the direction toward lid 10a on the inside of inserted part 10, causing the magnetic flux density at the end of magnetic forceps 1 to increase, and the magnetic force generated at the end of inserted part 10 to intensify.

Anchoring device 2 is provided with a magnet (magnetic body) 21 and a clip 20 that holds and is fixed in place to the mucosa on the inside of the stomach. Magnet 21 is connected to clip 20 via thread 22, and is coated with a material such as titanium or silicon that is not harmful to the body.

Magnetic forceps 1 is used in combination with a rigid sheath 3. Sheath 3 is cylindrical in form, and has an inner diameter that is slightly larger than the outer diameter of inserted part 10. Magnetic forceps 1 is inserted into the abdominal cavity while disposed inside sheath 3, and is employed in a state where the end of magnetic forceps 1 (i.e., the end of inserted part 10) projects out from sheath 3.

The surgical sequence will now be explained.

First, several days to several weeks prior to the surgery, anchoring device 2 is anchored in the stomach wall near the site where a lesion has occurred on the inside of the stomach. Specifically, an endoscope is inserted into the patient via the oral cavity, anchoring device 2 is introduced to the inside of the stomach by passing it through the inserted part of the endoscope, and the stomach wall near the lesion site is grabbed and held in place by clip 20. In order to prevent clip 20 from falling off, care is exercised to firmly grab the mucosa of the stomach wall with clip 20. Further, in order to appropriately resect the lesion during surgery, the positional relationship between the lesion site and the site where anchoring device 2 is anchored is recorded.

Next, the actual surgical sequence will be described.

The patient is placed in the supine position, and a laparoscopic trocar (an instrument used for introducing surgical instruments into the abdominal cavity) is inserted by piercing the abdominal wall at a site flanking the umbilicus. Carbon dioxide gas is injected into the abdominal cavity via the laparoscopic trocar, to insufflate the abdominal cavity and secure the surgical space. The position of insertion of the laparoscopic trocar is indicated by symbol A in FIG. 3. In addition, two trocars for the forceps and one trocar for procedure tools are each inserted by piercing through the abdominal wall. The positions for insertion of the trocars for the forceps are indicated by symbols B and C in FIG. 3, and the position of insertion of the trocar for the procedure tools is indicated by symbol D in the same figure.

The laparoscope is inserted into the abdominal cavity via the laparoscopic trocar. A television camera is connected to the laparoscope. The view from the endoscope, which is captured on this television camera, is projected on a television monitor that is disposed inside the operating room. The surgeon views the inside of the abdominal cavity by watching the image displayed on the television monitor. Further, grasping forceps and the procedure tools are inserted into the abdominal cavity via the other trocars, and peeling of the serosal membrane surrounding the stomach and duodenum, cutting of vessels and removal of lymph nodes are performed.

The duodenum is detached using a cutting tool while holding the lower portion of the stomach using the grasping forceps.

Figure 4:
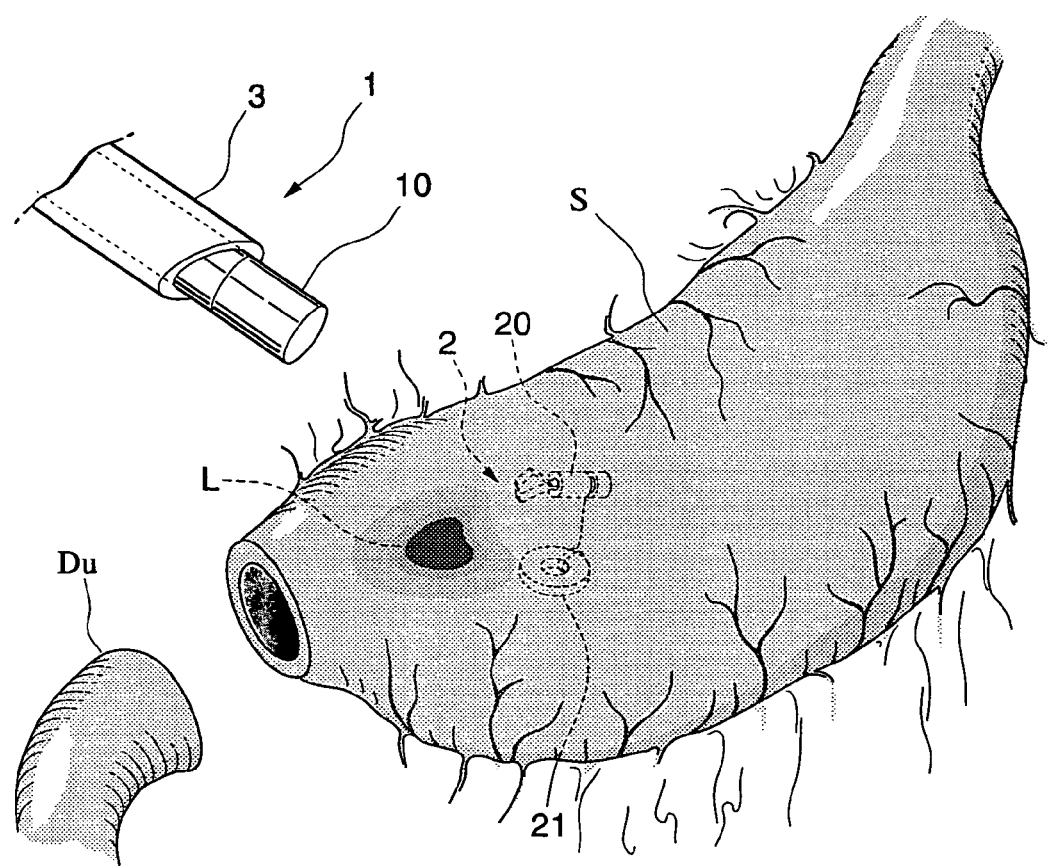
FIG. 4 is a phase diagram showing a process in the surgery for partial resection of the stomach according to the present invention.
Figure 5:
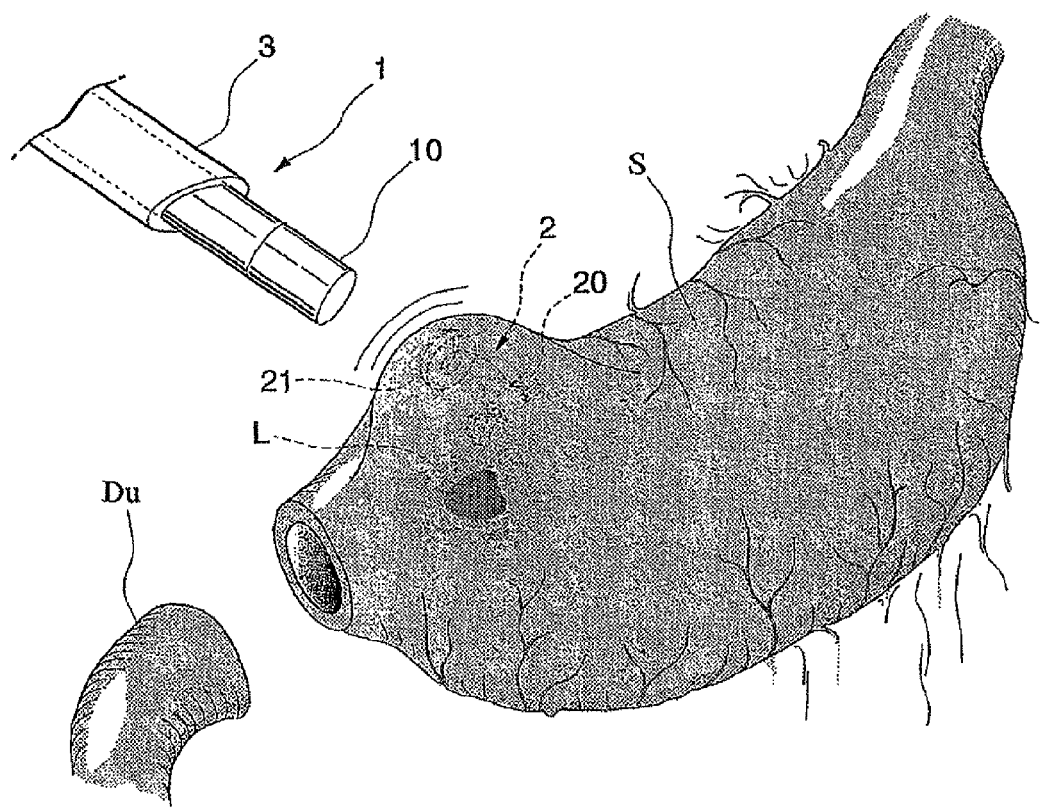
FIG. 5 is a phase diagram showing a process in the surgery for partial resection of the stomach according to the present invention.

Sheath 3 is inserted into the abdominal cavity via the forceps trocar. Next, as shown in FIG. 4, magnetic forceps 1 is inserted into the abdominal cavity through sheath 3. At this time, the magnetic force of magnetic forceps 1 is weak. When the end of magnetic forceps 1 is brought close to the outside of stomach S, the magnetic force of magnetic forceps 1 intensifies and, as shown in FIG. 5, magnet 21 of anchoring device 2 is attracted toward the end of magnetic forceps 1. As a result, the stomach wall where magnet 21 is anchored deforms so as to be lifted up toward the outside. The surgeon observes the change in the shape of the stomach wall from the image displayed on the television monitor, and acknowledges this site where anchoring device 2 is anchored. Then, based on the record of the positional relationship between lesion site L and the location at which anchoring device 2 is anchored, the surgeon estimates the position of lesion site L correctly. While the surgeon estimates the location of the lesion site L, the magnetic force of magnetic forceps 1 is increased, magnet 21 is pulled and held to the end of magnetic forceps 1 along with the stomach wall where lesion L has occurred, and the stomach wall is held with magnetic forceps 1.

Figure 6:
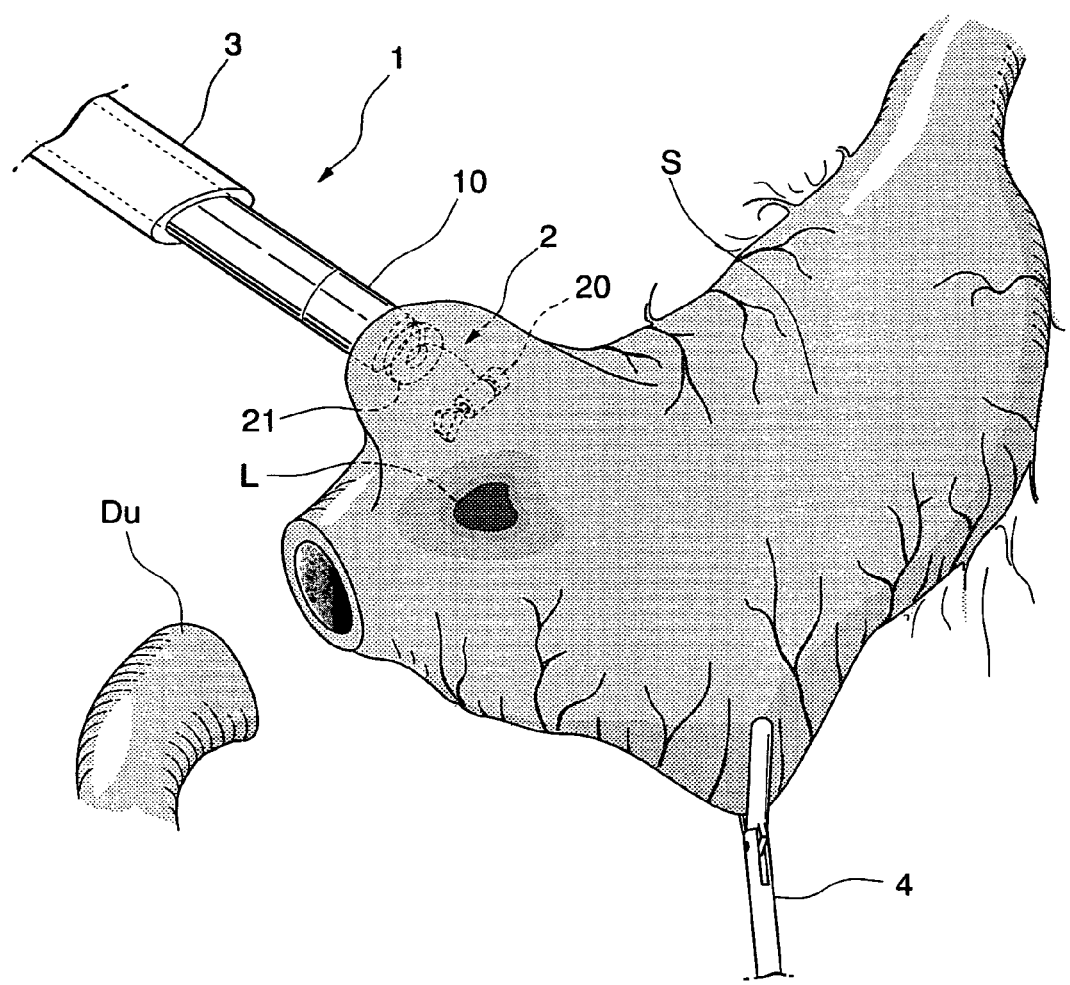
FIG. 6 is a phase diagram showing a process in the surgery for partial resection of the stomach according to the present invention.
Figure 7:
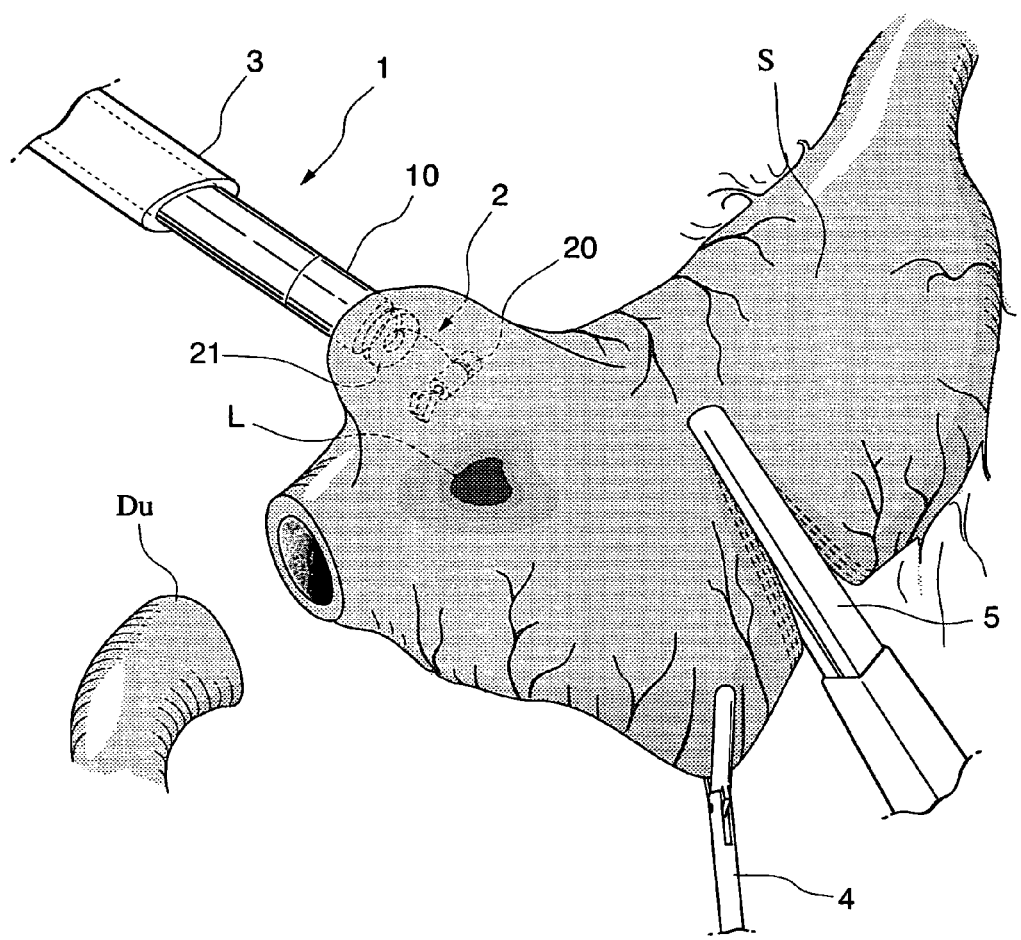
FIG. 7 is a phase diagram showing a process in the surgery for partial resection of the stomach according to the present invention.

While holding the stomach wall with magnetic forceps 1, another area of the stomach wall is held using grasping forceps 4, which were inserted into the abdominal cavity via another forceps trocar, as shown in FIG. 6. Stomach S is then held in two places using magnetic forceps 1 and grasping forceps 4, and an automatic suturing device 5 is employed to incise and suture stomach S, as shown in FIG. 7. The incised area is closer to the cardia than the areas being held by magnetic forceps 1 and grasping forceps 4, i.e., closer than the part that includes lesion site L, and lesion site L is included in this detached portion of the stomach.

Grasping forceps 4 is released from stomach S, and the detached portion of the stomach is pulled out from the abdominal cavity along with magnetic forceps 1. The penetrating hole though which magnetic forceps 1 was passed is enlarged, etc., to pull the detached stomach out of the abdominal cavity.

Figure 8:
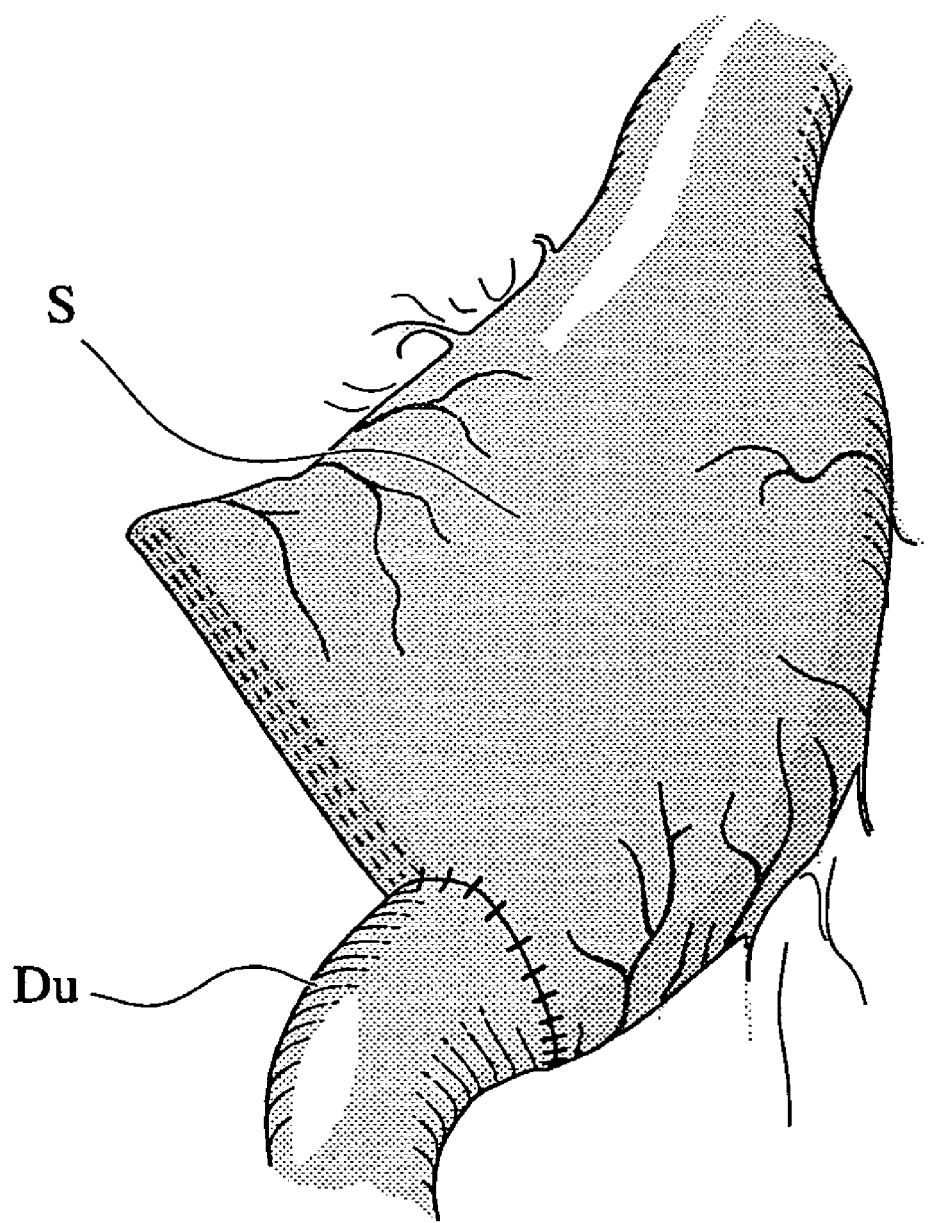
FIG. 8 is a phase diagram showing a process in the surgery for partial resection of the stomach according to the present invention.

In place of magnetic forceps 1, a regular grasping forceps is inserted into the abdominal cavity, and two grasping forceps are used to hold the remaining stomach and the duodenum. As shown in FIG. 8, only a portion of the sutured part of the remaining stomach S is then resected, and this resected part and the duodenum Du are anastomosed using an automatic anastomosing device. Note that it is also acceptable for the surgeon to perform the suturing, rather than using a procedure tool such as an automatic anastomosing device.

Once anastomosis is complete, the laparoscope, grasping forceps and other instruments are removed, a drain tube is passed through the penetrating hole that was used to pass the grasping forceps, the other penetrating holes are sutured closed, and the surgery is completed.

In the above-described surgery for partial resection of the stomach under laparoscopy, when the end of the magnetic forceps is brought close to the outside of the stomach, magnet 21 is attracted to the end of magnetic forceps 1, and the stomach wall in which magnet 21 is anchored is deformed so as to be lifted up toward the outside. As a result, the surgeon can correctly estimate the site where anchoring device 2 is fixed, i.e., the position of the lesion site, easily and quickly, through the television monitor.

When the magnetic force of magnetic forceps 1 is increased, since magnet 21 is pulled and held to the end of magnetic forceps 1 along with the stomach wall, it is possible to hold the stomach wall which is difficult to grasp with the grasping forceps, etc., easily and correctly, without causing injury.

By using magnetic forceps 1 in this way, since the surgical time is shortened, and there is no injury to the stomach wall or other body tissues, it is possible to reduce the surgical stress on the patient.

In this embodiment, the resected stomach, i.e., the portion of the stomach that includes the lesion, was removed prior to anastamosing stomach S and duodenum Du, however, it is also acceptable to remove this portion of the stomach after the anastamosis. In this case, after resecting the stomach, operating part 12 is manipulated to decrease the magnetic force of magnetic forceps 1, and the resected stomach is at once released from magnetic forceps 1. A regular grasping forceps is then inserted into the abdominal cavity in place of magnet forceps 1, and the stomach and duodenum are anastomosed in the same manner as above. Once the anastomosis is complete, magnetic forceps 1 is reinserted into the abdomen cavity in place of the regular grasping forceps. The end of magnetic forceps 1 is brought near the stomach (resected stomach) which was temporarily placed within the abdominal cavity, and the stomach is pulled and held to the end of magnetic forceps 1 as a result of the increase in magnetic force. The resected stomach is then pulled out along with magnetic forceps 1, and is withdrawn from the abdominal cavity by enlarging the penetrating hole through which the magnetic forceps 1 was passed.

Figure 9:
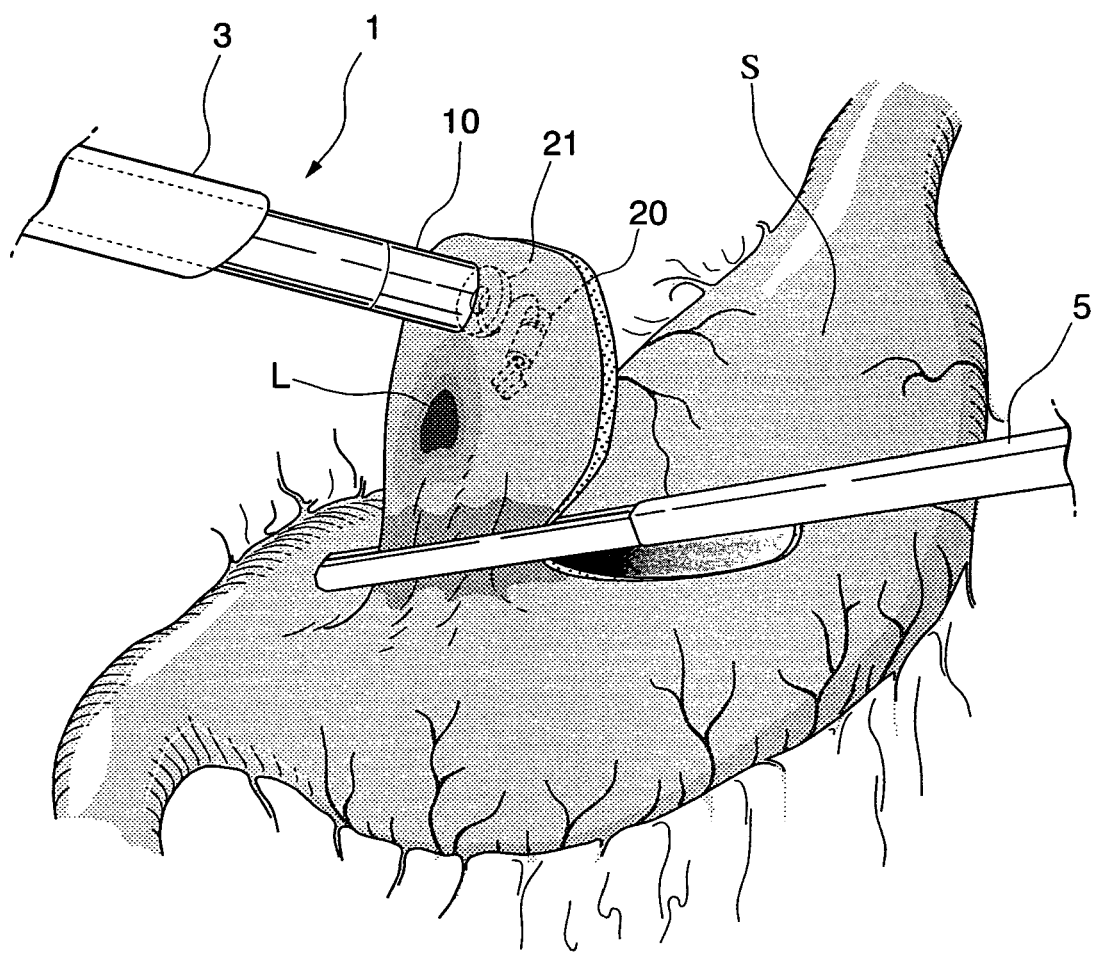
FIG. 9 is a phase diagram showing a different process from the above in the surgery for partial resection of the stomach according to the present invention.

In this embodiment, surgery to join the duodenum with the remaining portion of the stomach left after resection of the lower part of the stomach was explained. However, if the lesion site is not so large, then it is also acceptable to resect only the stomach wall where the lesion occurred, within given margins, as shown in FIG. 9.

Embodiment 2

In this embodiment, the surgery for partial resection of the large intestine will be explained with reference to FIGS. 10 through 13.

First, several days to several weeks prior to the surgery, anchoring device 2 is anchored in the intestinal wall near the site where a lesion has occurred on the inside of the large intestine. Specifically, an endoscope is inserted via the anus, anchoring device 2 is introduced to the inside of the large intestine by passing it through the inserted part of the endoscope, and the intestinal wall near the lesion site is grabbed and held by clip 20. In order to prevent clip 20 from falling off, care is exercised to ensure that clip 20 firmly grabs the mucosa of the intestinal wall. Further, in order to appropriately resect the lesion during surgery, the positional relationship between the lesion site and the site where anchoring device 2 is anchored is recognized.

Next, the actual surgical sequence will be explained.

A laparoscope is inserted into the patient's abdominal cavity. The surgeon views the inside of the abdominal cavity by watching the image displayed on the television monitor. Further, grasping forceps and procedure tools are inserted into the abdominal cavity. Peeling of the serosal membrane surrounding the large intestine, cutting of vessels and removal of lymph nodes are carried out.

Figure 10:
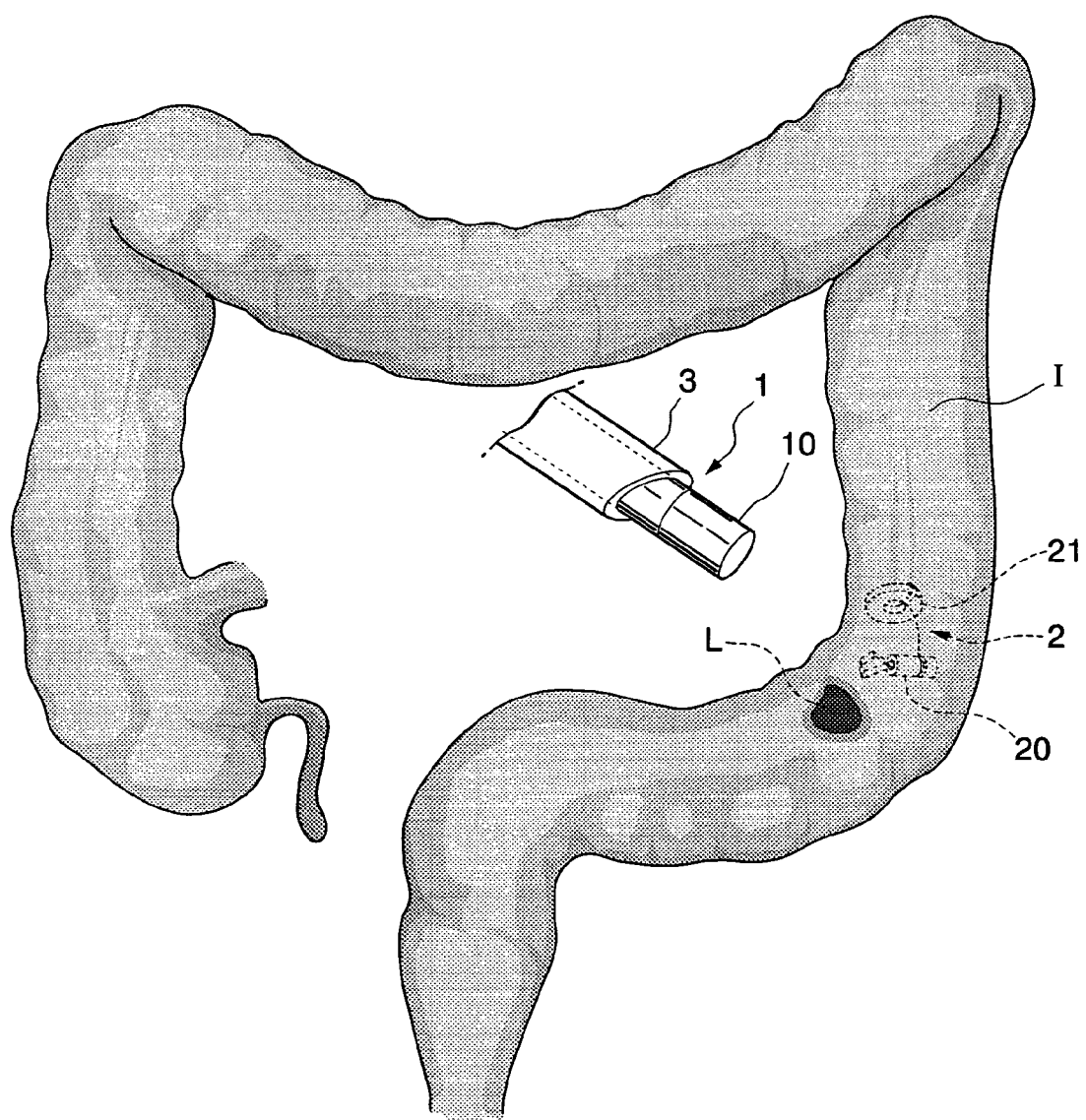
FIG. 10 is a phase diagram showing a process in the surgery for partial resection of the large intestine according to the present invention.

As shown in FIG. 10, sheath 3 is inserted into the abdominal cavity, and magnetic forceps 1 is then inserted into the abdominal cavity through sheath 3. At this time, the magnetic force of magnetic forceps 1 is set to be weak. When the end of magnetic forceps 1 is brought close to the outside of large intestine I, magnet 21 of anchoring device 2 is attracted to the end of magnetic forceps 1. As a result, the intestinal wall in which magnet 21 is anchored is deformed so as to be lifted up toward the outside. The surgeon observes the change in the shape of the intestinal wall from the image displayed on the television monitor, and acknowledges the site where anchoring device 2 is anchored. Based on the record of the positional relationship between lesion site L and the location at which anchoring device 2 is anchored, the surgeon estimates the position of lesion site L correctly. While the surgeon estimates the location of lesion site L, the magnetic force of magnetic forceps 1 is increased, magnet 21 is pulled and held to the end of magnetic forceps 1 along with the intestinal wall where lesion site L has occurred, and the intestinal wall is held with magnetic forceps 1.

Figure 11:
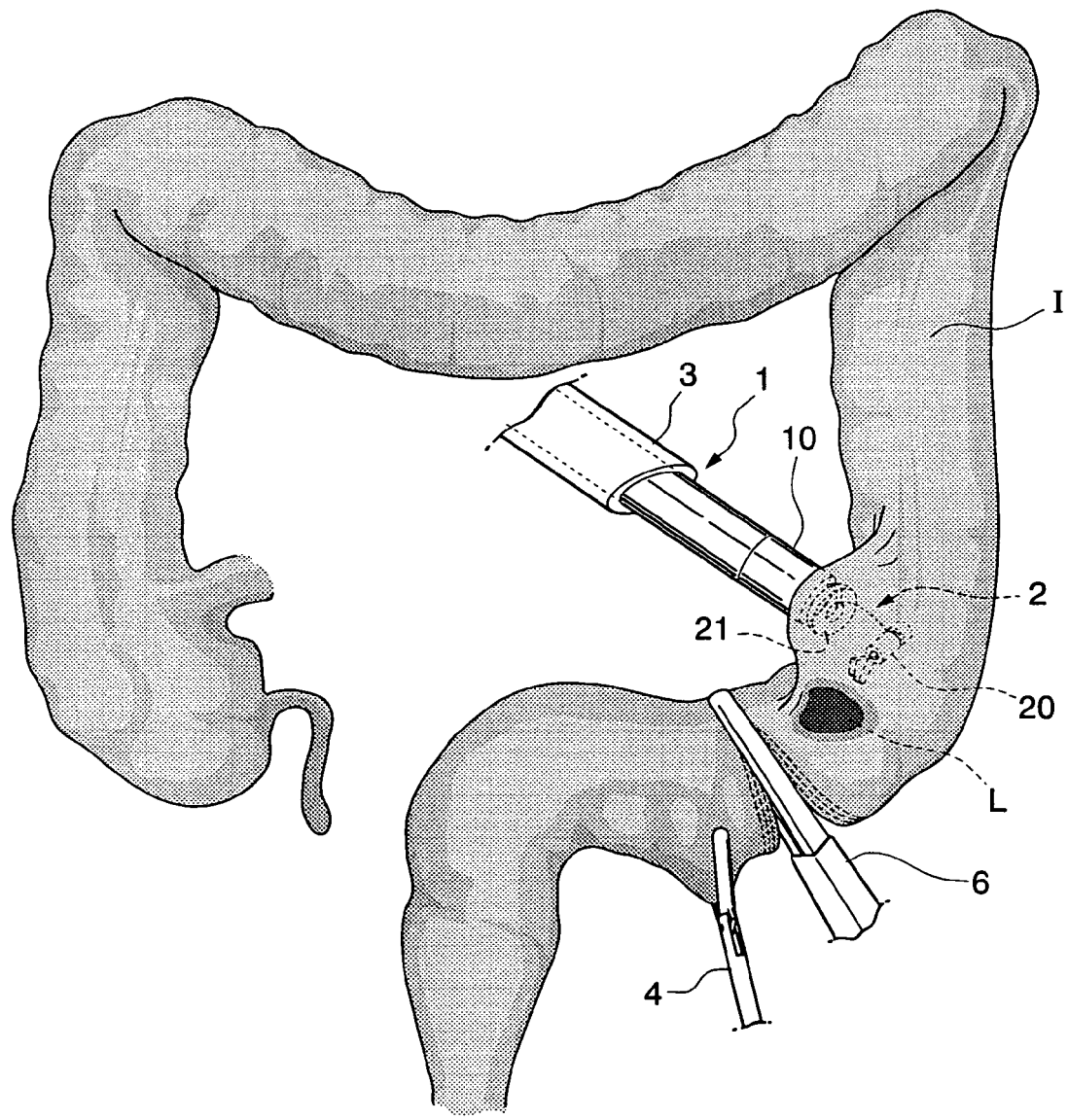
FIG. 11 is a phase diagram showing a process in the surgery for partial resection of the large intestine according to the present invention.

As shown in FIG. 11, while holding the intestinal wall with magnetic forceps 1, a part of the large intestine I that is closer to the anus than lesion site L is grasped using another grasping forceps 4 that was inserted into the abdominal cavity. Large intestine I is then detached using cutting tool 6, while being held in two places by magnetic forceps 1 and grasping forceps 4. The detached area is closer to the anus than the area being held by magnetic forceps 1, i.e., the area including lesion site L.

Figure 12:
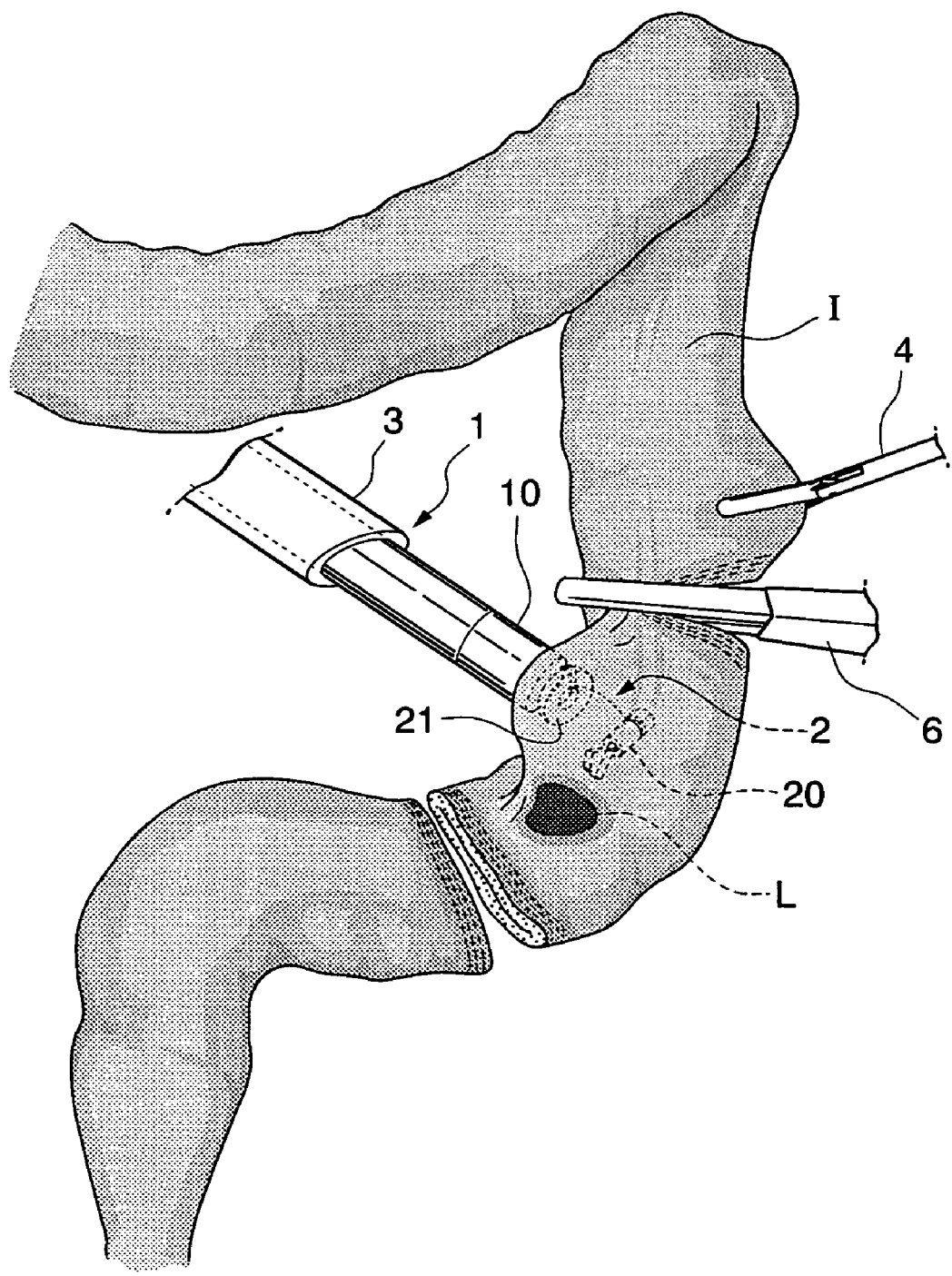
FIG. 12 is a phase diagram showing a process in the surgery for partial resection of the large intestine according to the present invention.

Next, while using magnetic forceps 1 to hold the intestinal wall where lesion site L has occurred, a part of the large intestine I that is closer to the mouth than lesion site L is held using grasping forceps 4 as shown in FIG. 12. The large intestine I is then detached using cutting tool 6 while being held at the two sites by magnetic forceps 1 and grasping forceps 4. The detached site is closer to the mouth than the part being held by magnetic forceps 1, i.e., the part including lesion site L.

Grasping forceps 4 is released from large intestine I, the resected large intestine is pulled out from the abdominal cavity along with magnetic forceps 1, and withdrawn from the abdominal cavity by widening the penetrating hole through which magnetic forceps 1 was passed. Note that the resected large intestine can also be withdrawn after anastamosis of the remaining intestine, in the same gist as described in the preceding first embodiment.

Figure 13:
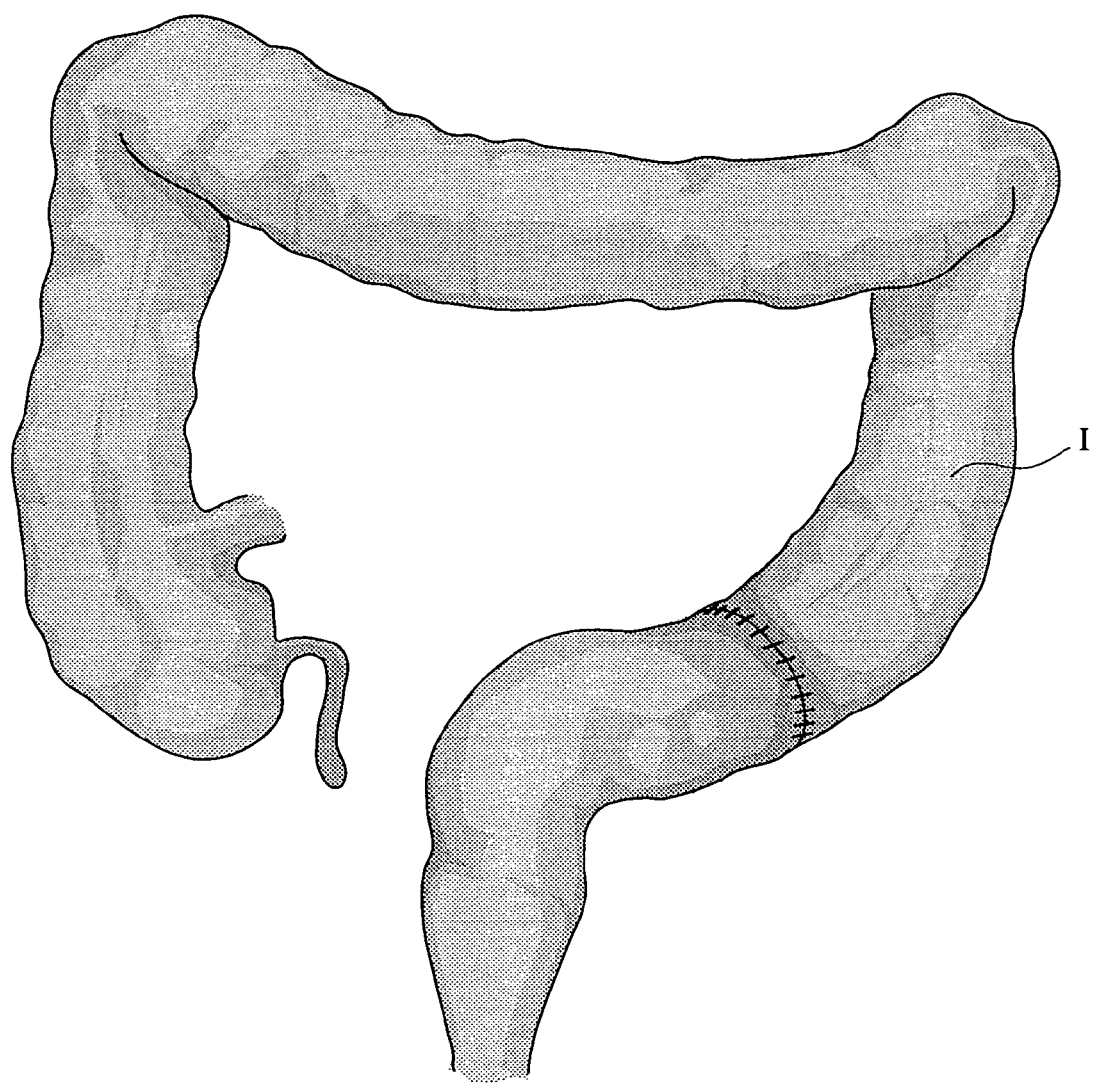
FIG. 13 is a phase diagram showing a process in the surgery for partial resection of the large intestine according to the present invention.

A regular grasping forceps is inserted into the abdominal cavity in place of magnetic forceps 1, the large intestine I on the oral side is held by one of the grasping forceps 4, and traction is applied toward the anus. Similarly, the large intestine I on the anal side is held by the other grasping forceps, and traction is applied toward the oral side. As shown in FIG. 13, the two pieces of large intestine held by grasping forceps 4 are then anastamosed using an automatic anastomosing device. Note that it is also acceptable for the surgeon to perform the suturing, rather than using a procedure tool such as an automatic anastomosing device.

Once the anastomosis is complete, the laparoscope, grasping forceps and other instruments are removed, a drain tube is passed through the penetrating hole that was used to pass the grasping forceps, the other penetrating holes are sutured closed, and the surgery is completed.

In the above-described surgery for partial resection of the large intestine under laparoscopy, the surgeon can correctly estimate the position of the lesion site, easily and quickly, through the television monitor.

When the magnetic force of magnetic forceps 1 is increased, since magnet 21 is adsorbed pulled and held to the end of magnetic forceps 1 along with the large intestine, it is possible to hold the large intestine which is difficult to grasp with the grasping forceps, etc., easily and correctly, without causing injury.

The preceding first and second embodiments employed a magnetic forceps 1 with a design for adjusting the strength of the magnetic force by moving a magnet 11 closer to or further away from the end of inserted part 10. However, it is also acceptable to employ a magnetic forceps using an electromagnet that is capable of electrically adjusting the magnetic force.

Instead of adjusting the magnetic force, it is also acceptable to prepare a plurality of magnetic forceps having different magnetic strengths. In this case, a forceps having a weak magnetic force is inserted into the abdominal cavity when acknowledging the lesion site, and is exchanged for a forceps having a strong magnetic force when holding the luminal organ where a lesion has occurred.

Surgery to resect a portion of the stomach or large intestine under laparoscopy was explained in the first and second embodiments above. However, these methods for probing and holding a luminal organ of the present invention are not limited to application under laparoscopy. Rather, these methods are also extremely effective and provide low stress on the patient in the case where probing or holding a luminal organ such as the stomach or large intestine during abdominal surgery. In this case, the holding position is not absolutely restricted to the lesion site or areas in the vicinity thereof. Rather, the aforementioned site may be anywhere that holding is necessary during surgery.

As explained above, in the present invention, when the magnet is brought close to the outside of a luminal organ, in which a magnetic body has been anchored on the inner surface thereof, the magnetic body is attracted to the magnet, and the wall of the luminal organ in which the magnetic body is anchored is deformed so as to lift up toward the outside. As a result, by observing this deformation from the outside of the luminal organ, it is possible to correctly estimate the site where the magnetic body is anchored easily and quickly.

Further, in the present invention, when the magnet is brought close to the outside of the luminal organ, in which a magnetic body has been anchored on the inner surface thereof, the magnetic body is attracted to the magnet, and the magnetic body is pulled and held to the magnet along with the wall of the luminal organ. It is possible to hold the body tissue which is difficult to grasp with the grasping forceps, etc., easily and correctly, without causing injury.

According to the present invention, it is possible to correctly estimate the position where the magnetic body is anchored easily and quickly, even from outside the luminal organ.

Further according to the present invention, it is possible to hold the body tissue which is difficult to grasp with the grasping forceps, etc., easily and correctly, without causing injury.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A method for probing a luminal organ comprising:
    pre-anchoring a magnetic body at a specific position inside a luminal organ within an abdominal cavity;
    bringing magnetic forceps within said abdominal cavity close to the outside of said luminal organ, such that said magnetic body inside said luminal organ is attracted to said magnetic forceps, along with the body tissue of said luminal organ;
    deforming said luminal organ to be lifted up toward outside of said luminal organ so as to observe the body tissue from outside of said luminal organ; and
    acknowledging the position of said magnetic body pre-anchored inside said luminal organ by visually observing said luminal organ which is deformed by the attraction of said magnetic body by said magnetic forceps.

2. A method for holding a luminal organ comprising:
    pre-anchoring a magnetic body at a specific position inside a luminal organ within an abdominal cavity;
    bringing magnetic forceps within said abdominal cavity close to the outside of said luminal organ, such that said magnetic body is pulled to said magnetic forceps, along with the body tissue of said luminal organ;
    deforming said luminal organ to be lifted up toward outside of said luminal organ so as to observe the body tissue from outside of said luminal organ; and
    holding the body tissue of said luminal organ between said magnetic forceps outside said luminal organ and said magnet body inside said luminal organ.

3. A method for changing between a body tissue attraction operation and a body tissue holding operation, the method comprising:
    pre-anchoring a magnetic body at a specific position inside a luminal organ within an abdominal cavity;
    performing the body tissue attraction operation by bringing a magnet within said abdominal cavity close to the outside of said luminal organ, such that said magnetic body inside said luminal organ is attracted to said magnet along with the body tissue of said luminal organ, and by deforming said luminal organ to be lifted up toward outside of said luminal organ so as to observe the body tissue from outside of said luminal organ;

performing the body tissue holding operation by pulling said magnetic body inside said luminal organ to said magnet along with the body tissue of said luminal organ, such that the body tissue is interposed between said magnet outside said luminal organ and said magnetic body inside said luminal organ; and using a plurality of magnetic forceps having different magnetic strengths so as to change between the body tissue attraction operation and the body tissue holding operation.

4. The method for probing a luminal organ according to claim 1, wherein said magnetic forceps is inserted into said abdominal cavity through a hole formed in an abdominal wall, and then is operated through the hole.

5. The method for holding a luminal organ according to claim 2, wherein said magnetic forceps is inserted into said abdominal cavity through a hole formed in an abdominal wall, and then is operated through the hole.

6. The method for changing between the applications according to claim 3, wherein said magnetic forceps is inserted into said abdominal cavity through a hole formed in an abdominal wall, and then is operated through the hole.

* * * * *